(12) United States Patent
Govari et al.

(10) Patent No.: US 6,498,477 B1
(45) Date of Patent: *Dec. 24, 2002

(54) MUTUAL CROSSTALK ELIMINATION IN MEDICAL SYSTEMS USING RADIATOR COILS AND MAGNETIC FIELDS

(75) Inventors: Assaf Govari, Haifa (IL); Shlomo Fried, Zichron Yaakov (IL)

(73) Assignee: Biosense, Inc., New Brunswick, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/702,974

(22) Filed: Oct. 31, 2000

Related U.S. Application Data

(63) Continuation-in-part of application No. 09/125,544, filed on Mar. 19, 1999, now Pat. No. 6,177,792.

(51) Int. Cl.$^7$ .................. G01B 7/004; G01R 33/025
(52) U.S. Cl. .................. 324/207.12; 324/207.17; 324/225
(58) Field of Search .................. 324/207.12, 207.17, 324/219, 220, 222, 225, 228, 229, 232, 233, 236–243, 260; 342/417, 418; 702/150

(56) References Cited

U.S. PATENT DOCUMENTS

| 3,644,825 A | 2/1972 | Davis, Jr. et al. ....... 324/207.26 |
| 3,868,565 A | 2/1975 | Kuipers ................. 324/207.26 |
| 4,017,858 A | 4/1977 | Kuipers ................. 342/350 |
| 4,054,881 A | 10/1977 | Raab ..................... 342/448 |
| 4,560,930 A | 12/1985 | Kouno .................. 324/207.17 |
| 4,613,866 A | 9/1986 | Blood ................... 342/448 |
| 4,642,786 A | 2/1987 | Hansen .................. 702/153 |
| 4,710,708 A | 12/1987 | Rorden et al. ........ 324/207.26 |
| 4,849,692 A | 7/1989 | Blood ................... 324/207.26 |
| 5,068,608 A | 11/1991 | Clark, Jr. ............... 324/220 |
| 5,211,165 A | 5/1993 | Dumoulin et al. ........ 600/410 |
| 5,253,647 A | 10/1993 | Takahashi et al. ........ 600/424 |
| 5,383,874 A | 1/1995 | Jackson et al. ........... 606/1 |
| 5,391,199 A | 2/1995 | Ben-Haim .............. 607/122 |
| 5,429,132 A | 7/1995 | Guy et al. .............. 600/422 |
| 5,443,489 A | 8/1995 | Ben-Haim .............. 607/115 |
| 5,453,687 A | 9/1995 | Zierdt et al. ........... 324/207.17 |
| 5,558,091 A | 9/1996 | Acker et al. ............ 600/424 |
| 5,577,502 A | 11/1996 | Darrow et al. .......... 600/426 |
| 5,715,822 A | 2/1998 | Watkins et al. .......... 600/422 |
| 5,729,129 A | 3/1998 | Acker ................... 324/207.12 |

FOREIGN PATENT DOCUMENTS

| EP | 0339723 A1 | 11/1989 |
| WO | WO 94/04938 A1 | 3/1994 |
| WO | WO 94/23647 A1 | 10/1994 |
| WO | WO 96/41119 A1 | 12/1996 |
| WO | WO 97/29685 A1 | 8/1997 |
| WO | WO 97/29709 A1 | 8/1997 |
| WO | WO 97/32179 A1 | 9/1997 |

*Primary Examiner*—Edward Lefkowitz
*Assistant Examiner*—Reena Aurora
(74) *Attorney, Agent, or Firm*—Louis J. Capezzuto (57) ABSTRACT

Apparatus for generating magnetic fields includes a plurality of radiator coils. Driver circuitry drives the coils so as to generate magnetic fields at a plurality of driving frequencies. Each of the coils is driven by a respective current that comprises a basic current at a respective one of the driving frequencies and cancellation currents at one or more of the other driving frequencies, so that each of the radiator coils generates a field substantially only at the respective driving frequency.

12 Claims, 4 Drawing Sheets

MUTUAL CROSSTALK ELIMINATION IN MEDICAL SYSTEMS USING RADIATOR COILS AND MAGNETIC FIELDS

CROSS-REFERENCE TO RELATED APPLICATIONS

This application is a continuation-in-part of U.S. patent application Ser. No. 09/125,544 filed Mar. 19, 1999, which is assigned to the assignee of the present patent application and whose disclosure is incorporated herein by reference.

FIELD OF THE INVENTION

The present invention relates generally to apparatus for generating and detecting electromagnetic fields, and specifically to non-contact, electromagnetic methods and devices for tracking the position and orientation of an object.

BACKGROUND OF THE INVENTION

Non-contact electromagnetic tracking systems are well known in the art, with a wide range of applications.

For example, U.S. Pat. No. 4,054,881, whose disclosure is incorporated herein by reference, describes a tracking system using three coils to generate electromagnetic fields in the vicinity of the object. The fields generated by these three coils are distinguished from one another by open loop multiplexing of time or frequency. The signal currents flowing in three orthogonal sensor coils are used to determine the object's position, based on an iterative method of computation.

U.S. Pat. No. 5,391,199, whose disclosure is incorporated herein by reference, describes a system for generating three-dimensional location information regarding a medical probe or catheter. A sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT patent application number PCT/US95/01103 and the corresponding U.S. national phase patent application Ser. No. 08/793,371, whose disclosures are incorporated herein by reference, describe a system that generates six-dimensional position and orientation information regarding the tip of a catheter. This system uses a plurality of non-concentric sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates. The radiator coils operate simultaneously at different frequencies, for example at 1000, 2000 and 3000 Hz, respectively.

Other position sensing systems use a single coil in the catheter. The signals from the coil are sufficient, in conjunction with multiple field generator coils, to generate three dimensions of position and two dimensions of orientation information. The third dimension of orientation (typically rotation of the catheter about its longitudinal axis) can be inferred if needed from a comparison of the coordinates of two such sensors provided at mutually-spaced locations in the catheter and/or from mechanical information.

The above tracking systems rely on separation of position-responsive signals into frequency components, wherein each such component is assumed to correspond uniquely to a single radiator coil, in a known position, radiating in a narrow, well-defined frequency band. In practice, however, the radiator coils also generate magnetic fields at the frequencies outside the desired bands, for example due to mutual inductance effects. These mutually-induced fields lead to errors in determining the position of the object being tracked.

PCT patent application PCT/IL97/00100 and the above-mentioned U.S. patent application Ser. No. 09/125,544 describe apparatus for generating magnetic fields with reduced mutual inductance effects. The apparatus includes a plurality of radiator coils and driver circuitry coupled thereto, which drives the coils so as to generate magnetic fields at a plurality of driving frequencies. The radiator coils are configured and controlled so that each of them generates a field substantially only at a single, respective driving frequency. Preferably, circuitry is associated with at least one of the plurality of radiator coils for substantially eliminating magnetic fields generated by the at least one coil in response to fields generated by the other coils.

SUMMARY OF THE INVENTION

It is an object of some aspects of the present invention to provide improved electromagnetic radiator coils and driver circuitry therefor, for use in conjunction with object tracking systems in order to increase the accuracy of object tracking.

It is a further object of some aspects of the present invention to provide magnetic field generator coils and associated driver circuitry that generate fields having narrow bandwidths in the frequency domain.

In one aspect of the present invention, narrowed field bandwidth is achieved by canceling out mutual inductance effects among a plurality of coils, which generate magnetic fields at different frequencies.

In preferred embodiments of the present invention, a plurality of radiator coils generate magnetic fields at a plurality of different respective driving frequencies. Driver circuitry associated with the coils generates electrical driver currents therein, wherein for each coil the current comprises a major component at the coil's respective driving frequency, and minor components at other frequencies. Typically, the minor components are substantially equal in amplitude and frequency and 180° out of phase with parasitic currents induced in the coil due to magnetic fields generated by the other radiator coils, so as to substantially cancel the effect of the induced currents.

Preferably, the driver circuitry includes sensing apparatus, which measures the amplitude, frequency and phase of the induced parasitic currents in a the coil. The driver circuitry further includes an adaptive variable current supply, which generates the out-of-phase minor current components responsive to the amplitude, frequency and phase data measured by the sensing apparatus, so as to substantially cancel the effect of the induced parasitic currents. Most preferably, the process of measuring the parasitic currents and adjusting the minor current components is repeated iteratively until the amplitude of the parasitic components is reduced to below a predetermined threshold level.

There is therefore provided, in accordance with a preferred embodiment of the present invention, apparatus for generating magnetic fields, including:

a plurality of radiator coils; and driver circuitry, coupled thereto, which drives the coils so as to generate magnetic fields at a plurality of driving frequencies, such that each of the coils is driven by a respective current that includes a basic current at a respective one of the driving frequencies and cancellation currents at one or more of the other driving frequencies, so that each of the radiator coils generates a field substantially only at the respective driving frequency.

Preferably, the cancellation currents are determined so as to substantially cancel parasitic magnetic fields generated by each of the coils in response to the magnetic fields generated by the other coils at the respective driving frequencies of the other coils. Most preferably, the cancellation currents are generated by the driver circuitry so as to be, in each of the coils, approximately equal in amplitude and opposite in phase to parasitic currents generated in the coil due to the magnetic fields generated by the other coils at the respective driving frequencies of the other coils.

In a preferred embodiment, the driver circuitry includes a current analyzer, which is coupled to measure parasitic currents flowing in each of the coils at the respective driving frequencies of the other coils, and wherein the driver circuitry is adapted to generate the cancellation currents responsive to the measured parasitic currents. Preferably, the driver circuitry includes an adaptive current supply, which is driven by the current analyzer to generate the cancellation currents. Alternatively or additionally, the driver circuitry includes a memory, which is adapted to store, for each of the coils, data indicative of a waveform of the respective current with which the coil is to be driven, and wherein the data are modified responsive to the measured parasitic currents. Most preferably, the driver circuitry is adapted to adjust the generated respective current in each coil so as to minimize the parasitic electrical current measured therein.

There is also provided, in accordance with a preferred embodiment of the present invention, a method for generating a magnetic field having a desired narrow frequency band, including:

driving a radiator coil with an electrical current at a frequency in the desired narrow frequency band;

analyzing the current flowing in the coil to measure induced current components at one or more undesired frequencies; and adjusting the current driving the coil so as to include correction current components at the one or more undesired frequencies, responsive to the measured induced current components, so that the coil generates a field substantially only at the respective driving frequency.

There is additionally provided, in accordance with a preferred embodiment of the present invention, a method for tracking an object, including:

driving a plurality of radiator coils with electrical currents at respective driving frequencies so as to generate a plurality of magnetic fields at the frequencies in a vicinity of an object being tracked;

analyzing the currents flowing in the coils so as to measure, in each of the coils, induced current components at one or more of the frequencies of the other coils;

adaptively adjusting the current driving each of the coils so as to include correction current components at the frequencies of the other coils, responsive to the measured induced current components, so that each of the coils generates a field substantially only at the respective driving frequency;

placing one or more sensor coils at a locatable site on the object; receiving signals generated by the sensor coils in response to the magnetic fields; and analyzing the signals to determine position and orientation coordinates of the object.

There is further provided, in accordance with a preferred embodiment of the present invention, an object tracking system, including:

a plurality of radiator coils; and driver circuitry, coupled to drive the coils to generate magnetic fields at a plurality of driving frequencies, such that each of the coils is driven by a respective current that includes a basic current at a respective one of the driving frequencies and cancellation currents at one or more of the other driving frequencies, so that each of the coils generates a field substantially only at the respective driving frequency;

one or more sensor coils, fixed to the object; and processing circuitry, coupled to receive and analyze currents induced in the sensor coils due to the magnetic fields, so as to determine coordinates of the object. The present invention will be more fully understood from the following detailed description of the preferred embodiments thereof, taken together with the drawings in which:

DETAILED DESCRIPTION OF PREFERRED EMBODIMENTS

Figure 1:
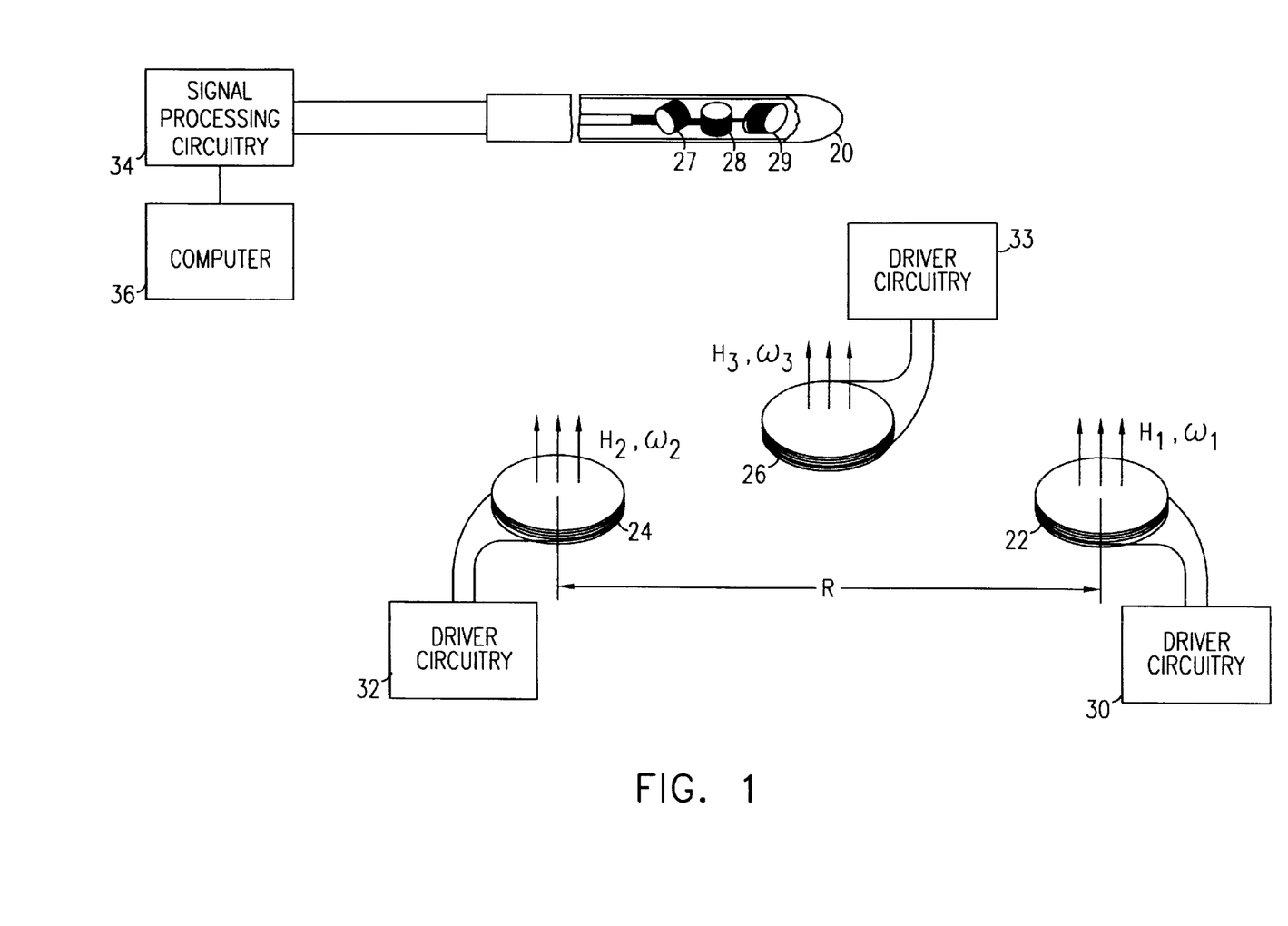
FIG. 1 is a schematic representation of an object tracking system, operative in accordance with a preferred embodiment of the present invention.

Reference is now made to FIG. 1, which illustrates schematically a system for tracking a probe 20, such as a catheter for medical use, operative in accordance with preferred embodiment of the present invention. As described in the above-mentioned U.S. Pat. No. 5,391,199, to Ben-Haim, and PCT patent application PCT/US95/01103, the system comprises a plurality of radiator coils 22, 24 and 26. These coils generate respective magnetic fields $H_1$, $H_2$ and $H_3$, at respective frequencies $\omega_1$, $\omega_2$, and $\omega_3$, in the vicinity of probe 20. The probe further includes sensor coils 27, 28 and 29, which generate electrical current signals in response to the magnetic fields, wherein the signals comprise components at frequencies $\omega_1$, $\omega_2$, and $\omega_3$, whose respective amplitudes are dependent on the position and orientation of probe 20.

The system further comprises driver circuitry 30, 32 and 33, coupled to each of the radiator coils, which drives coils 22, 24 and 26 at respective driving frequencies $\omega_1$, $\omega_2$, and $\omega_3$. The signals generated by sensor coils 27, 28 and 29 are preferably processed by signal processing circuitry 34 and then used by computer 36 to calculate position and orientation coordinates of probe 20.

For the sake of clarity, FIG. 1 shows three radiator coils 22, 24 and 26 and three sensor coils 27, 28 and 29 in a probe 20. It will be understood, however, that the present invention is equally applicable to tracking systems comprising two, four or more radiator coils and one, two or more sensor coils. The present invention may be used in tracking other types of objects, as well.

In the absence of mutual inductance effects, the signals generated by sensor coils 27, 28 and 29 at frequency $\omega_1$ are proportional to the amplitude of the time derivative of the projection of magnetic flux due to field $H_1$ at probe 20 along each of the respective axes of the sensor coils. The signals generated at frequencies $\omega_2$ and $\omega_3$ are similarly proportional to the projections of $H_{2\ and\ H3}$. Since the direction and amplitude of the magnetic field due to a single such radiator coil can be calculated easily using methods known in the art, the sensor coil signals due to a single radiator coil may be directly related to the sensor coil's distance from and orientation relative to the radiator coil.

In practice, however, magnetic field $H_1$ generated by radiator coil 22 is not limited in space to an immediate vicinity of probe 20, but also has a non-zero amplitude in a vicinity of coils 24 and 26. As is known in the art, there is a mutual inductance $M_{12}$ between coils 22 and 24, which causes an additional, parasitic current $I_{12}$ at frequency $\omega_1$ to flow in coil 24 due to field $H_1$, and likewise causes a parasitic current $I_{21}$ in coil 22 at frequency $\omega_2$. The amplitudes of the total currents $I_1$ and $I_2$ flowing in coils 22 and 24 are given generally by:

$$\begin{pmatrix} I_1 \\ I_2 \end{pmatrix} = \begin{pmatrix} L_1 & M_{12} \\ M_{12} & L_2 \end{pmatrix} \begin{pmatrix} \dot{V}_1 \\ \dot{V}_2 \end{pmatrix} \qquad (1)$$

Here $L_1$ and $L_2$ are the respective inductances of coils 22 and 24, while $\dot{V}_1$ and $\dot{V}_2$ are the time derivatives of the voltages in the coils. The theory of mutual inductance and its application in position sensing systems are further described in the above-mentioned PCT patent application PCT/IL97/00100.

The parasitic current $I_{12}$ flowing in radiator coil 24 ($I_{12}=M_{12}\dot{V}_1$) causes a parasitic magnetic field $H_{12}$ to be generated at frequency $\omega_1$, whose amplitude will be approximately proportional to the ratio $M_{12}/L_2$ when $\omega_1 \approx \omega_2$. $M_{12}$ depends on geometrical factors, including the orientations of and distance between the coils, as well as on parameters of coil construction. In tracking systems such as those described in U.S. Pat. No. 5,391,199 and in PCT patent application PCT/US95/01103, the amplitude of the parasitic current $I_{12}$ is typically on the order of 0.5% of the basic current $I_2$. Thus, the signals generated by sensor coils 27, 28 and 29 at frequency $\omega_1$ will include both a position signal component due to $H_1$ and a parasitic signal component due to $H_{12}$, which may introduce errors of up to 1% in determination of the field at probe 20. These errors may result in deviations of one to a few millimeters in determining the position of the probe. Additional parasitic signal components at frequency $\omega_1$ will be introduced by mutual inductance in coil 26 and any other radiator coils. Similarly, sensor coil signals at frequencies $\omega_2$ and $\omega_3$ will also include parasitic components.

Figure 2A:
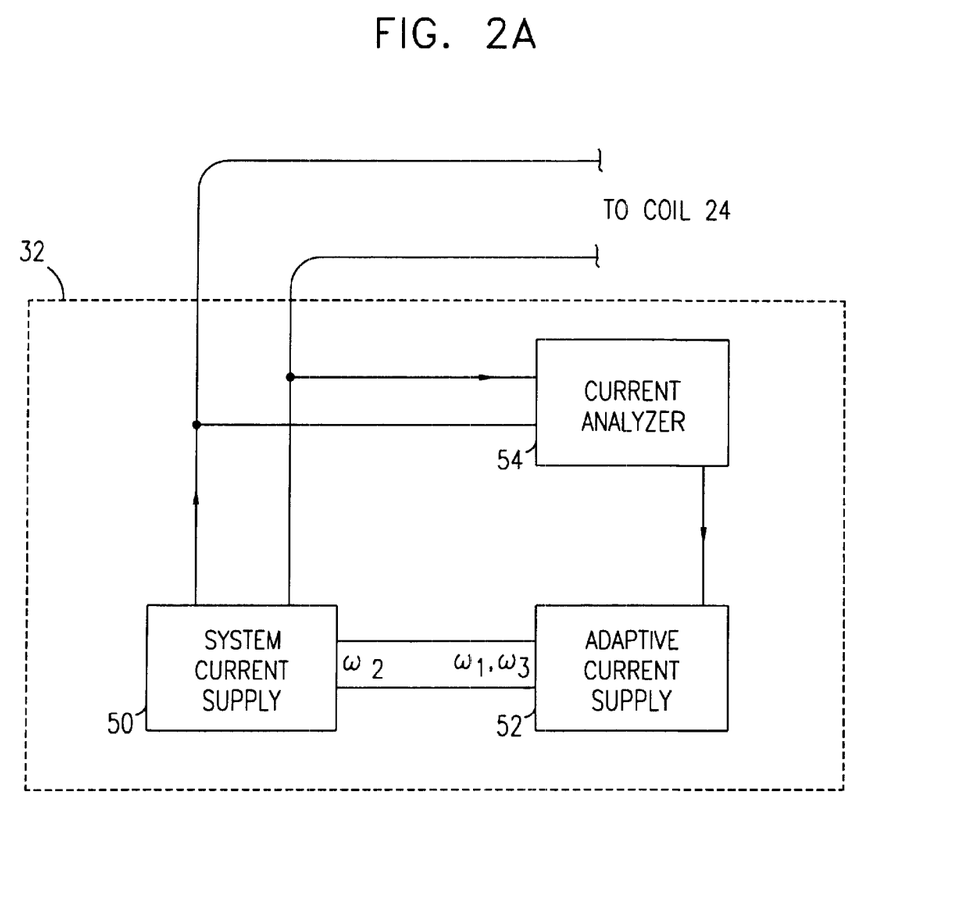
FIG. 2A is a block diagram that schematically illustrates coil driver circuitry, in accordance with another preferred embodiment of the present invention.

FIG. 2A illustrates schematically a preferred embodiment of the present invention, wherein driver circuitry 32 is adapted to drive coil 24 so as to substantially cancel mutually-induced currents. Circuitry 32 comprises a system current supply 50, which drives coil 24 at its driving frequency $\omega_2$, and adaptive current supply 52, which generates a correction current to drive coil 24 at the respective frequencies of coils 22 and 26, $\omega_1$ and $\omega_3$, with amplitudes and phases determined by a current analyzer 54. The current analyzer samples the current in coil 24, using methods known in the art, and separates the sampled current into frequency components. Analyzer 54 causes adaptive supply 52 to adjust the amplitudes and phases of the generated $\omega_1$ and $\omega_3$ currents so as to minimize the components sensed at these frequencies in the sampled current from coil 24. Typically the generated $\omega_1$ and $\omega_3$ correction currents are substantially approximately equal in amplitude to and 180° out of phase with the mutually-induced currents $I_{12}$ and $I_{32}$. A method for determining the correction currents is described hereinbelow with reference to FIG. 3. Coils 22 and 26 are driven by similar adaptive driver circuitry.

Figure 2B:
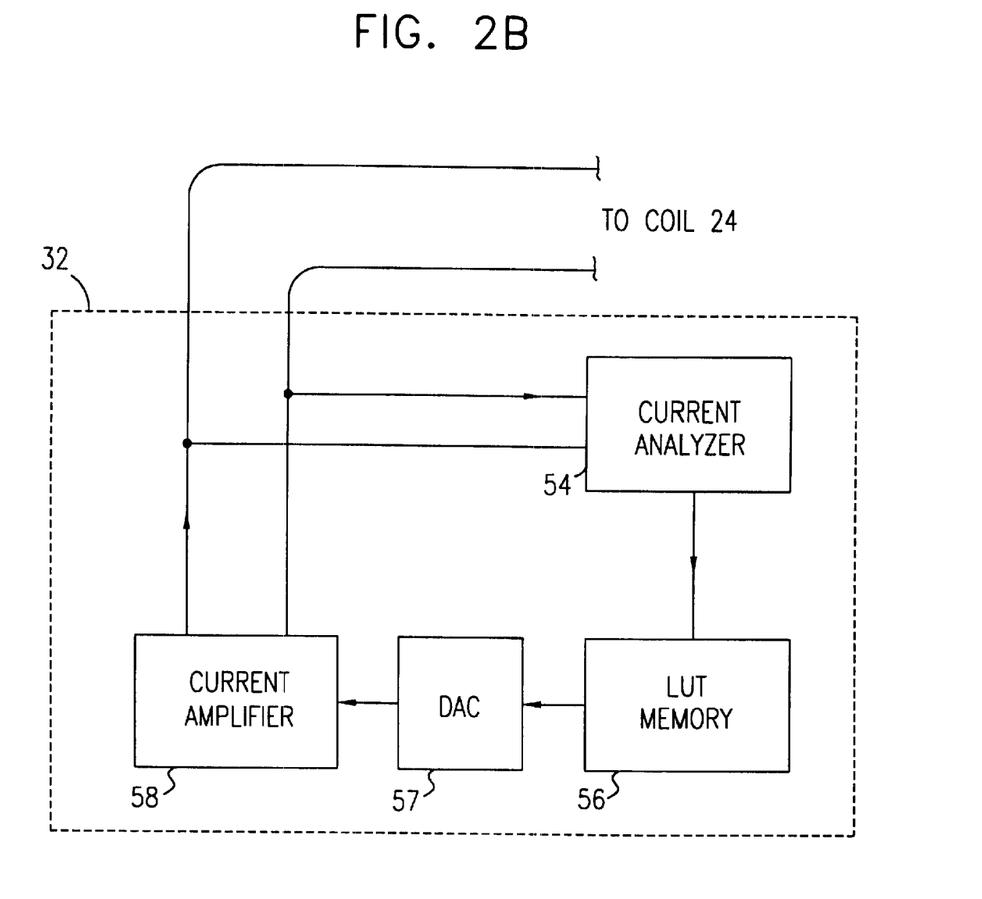
FIG. 2B is a block diagram that schematically illustrates coil driver circuitry, in accordance with another preferred embodiment of the present invention.

FIG. 2B is a block diagram that schematically illustrates driver circuitry 32, in accordance with an alternative embodiment of the present invention. In this case, the current driven through coil 24 is digitally controlled, based on waveform data stored in a memory look-up table (LUT) 56. The data in LUT 56 are read out in sequence to a digital/analog converter (DAC) 57, preferably an eight-bit DAC, in order to generate a waveform of the appropriate shape, with the desired frequency components. A current amplifier 58 filters and amplifies the waveform into the coil. Current analyzer 54 calculates the amplitude and phase of the required $\omega_1$ and $\omega_3$ correction current components, and digitally adds these components to the values in LUT 56.

Figure 3:
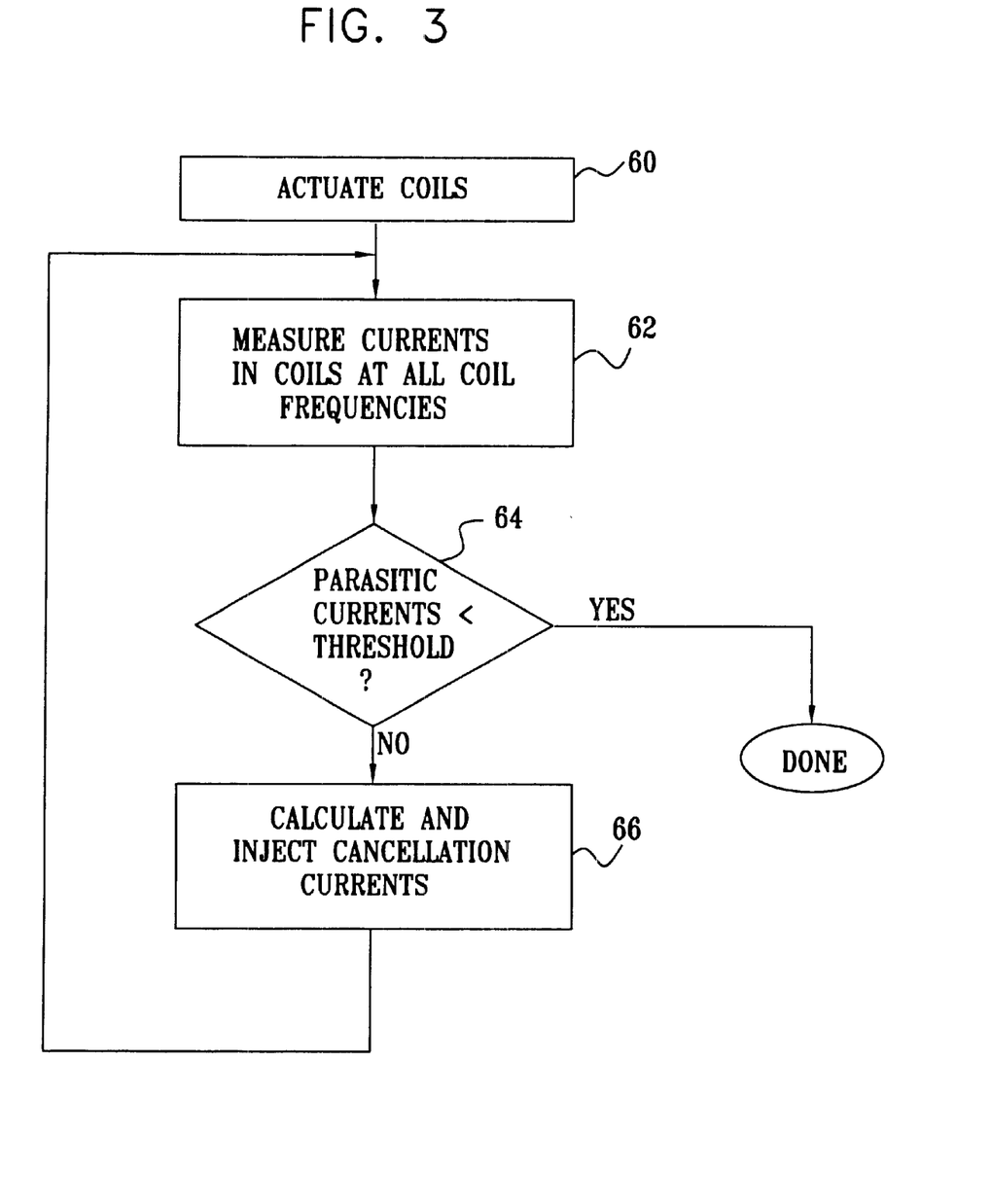
FIG. 3 is a flow chart illustrating schematically a method for adjusting the circuitry of FIG. 2A or 2B, in accordance with a preferred embodiment of the present invention.

FIG. 3 is a flow chart that schematically illustrates a method for determining the correction current components to be injected by driver circuitry 30, 32 and 33, in accordance with a preferred embodiment of the present invention. As in the preceding embodiments, the method is described here for convenience with respect to correction for the parasitic current generated in coil 24 at frequency $\omega_1$. At an actuation step 60, coils 22 and 24 (and typically, coil 26, as well) are actuated by their respective driver circuitry, such that each coil operates at its basic frequency. At a measurement step 62, current analyzer 54 measures the current flowing in coil 24 at the operating frequencies of all of the coils. The parasitic current $I_{12}$ in coil 24 is compared to the basic current $I_2$, at a comparison step 64. As noted above, the ratio of these currents before correction will typically be as high as 0.5%. For optimal tracking accuracy, the ratio should be no more than 0.1%.

Assuming it is necessary to reduce the parasitic currents in coil 24, a cancellation current in calculated, based on the measured current amplitude and phase, at a cancellation step 66. In calculating the cancellation current, it should be taken into account that coil 24 and circuitry 32 are preferably designed to be in resonance at frequency $\omega_2$. Therefore, when coil 24 is driven at frequency $\omega_1$ with a given driving voltage, the current in the coil will be reduced by a rejection factor T, given by:

$$T = \frac{R\omega_1 C}{\sqrt{(1-\omega_1^2 LC)^2 + \omega_1^2 C^2 R^2}} \qquad (2)$$

when compared with the current generated when the coil is driven by the same voltage at frequency $\omega_2$. Here R and L are the resistance and inductance, respectively, of coil 24, and C is the capacitance of circuitry 32. If the measured parasitic current at frequency $\omega_1$ is $I_{12}$, then a correction current should be added with amplitude $T^*I_{12}$, and a phase shift of 180°. Accordingly, current supply 52 is adjusted (in the embodiment of FIG. 2A), or the entries in LUT 56 are recalculated (in the embodiment of FIG. 2B).

Steps 62 and 64 are now repeated. Ideally, the parasitic currents now measured in coil 24 should be zero. In practice, however, some residual parasitic current is likely to remain. One of the causes of this residual current is double crosstalk between coils 22 and 24, wherein the correction current in coil 24 induces an additional current in coil 22 at its resonance frequency $\omega_1$, which then feeds back to coil 24. Therefore, steps 66, 62 and 64 are preferably repeated iteratively until the ratio of the parasitic currents to the basic current in each of the coils, at its respective frequency, converges to below the threshold mentioned above.

Although in the embodiments of FIGS. 2A and 2B, the functions of measuring the parasitic currents and determining the corrections to be applied for them are carried out within circuitry 30, 32 and 33, some or all of these operations may also be performed centrally, by computer 36, for example. Furthermore, other methods may be used for detecting and measuring the parasitic currents, such as analyzing the signals received from coils 27, 28 and 29, as described in the above-mentioned PCT patent application PCT/IL97/00100.

It will also be understood that while preferred embodiments are described with herein with reference to a system comprising three radiator coils and three sensor coils, it the principles of the present invention may equally be applied to other electromagnetic object tracking system, using greater or fewer numbers of coils or antennae.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed:

1. Apparatus for generating magnetic fields, comprising:
   a plurality of radiator coils; and driver circuitry, coupled thereto, which drives the coils so as to generate magnetic fields at a plurality of driving frequencies, such that each of the coils is driven by a respective current that comprises a basic current at a respective one of the driving frequencies and cancellation currents at one or more of the other driving frequencies, so that each of the radiator coils generates a field substantially only at the respective driving frequency, wherein the cancellation currents are determined so as to substantially cancel parasitic magnetic fields generated by each of the coils in response to the magnetic fields generated by the other coils at the respective driving frequencies of the other coils.

2. Apparatus in accordance with claim 1, wherein the cancellation currents are generated by the driver circuitry so as to be, in each of the coils, approximately equal in amplitude and opposite in phase to parasitic currents generated in the coil due to the magnetic fields generated by the other coils at the respective driving frequencies of the other coils.

3. Apparatus in accordance with claim 1, wherein the driver circuitry comprises a current analyzer, which is coupled to measure parasitic currents flowing in each of the coils at the respective driving frequencies of the other coils, and wherein the driver circuitry is adapted to generate the cancellation currents responsive to the measured parasitic currents.

4. Apparatus in accordance with claim 3, wherein the driver circuitry comprises an adaptive current supply, which is driven by the current analyzer to generate the cancellation currents.

5. Apparatus in accordance with claim 3, wherein the driver circuitry comprises a memory, which is adapted to store, for each of the coils, data indicative of a waveform of the respective current with which the coil is to be driven, and wherein the data are modified responsive to the measured parasitic currents.

6. Apparatus in accordance with claim 3, wherein the driver circuitry is adapted to adjust the generated respective current in each coil so as to minimize the parasitic electrical current measured therein.

7. A method for generating a magnetic field having a desired narrow frequency band, comprising:
   driving a radiator coil with an electrical current at a frequency in the desired narrow frequency band;
   analyzing the current flowing in the coil to measure induced current components at one or more undesired frequencies caused by at least one other radiator coil; and
   adjusting the current driving the coil so as to include correction current components at the one or more undesired frequencies, responsive to the measured induced current components, so that the coil generates a field substantially only at the respective driving frequency wherein the correction current components are cancellation currents determined so as to substantially cancel parasitic magnetic fields generated by the at least one other radiator coil.

8. A method according to claim 7, wherein adjusting the current comprises generating correction current components that are approximately equal in amplitude and opposite in phase to the induced current components measured at the respective one or more undesired frequencies.

9. A method in accordance with claim 7, wherein driving the radiator coil comprises storing data indicative of a waveform of the current with which the coil is to be driven, and wherein adjusting the current comprises modifying the data responsive to the induced current components.

10. A method in accordance with claim 7, and comprising iteratively repeating the steps of analyzing the current to measure the components at the undesired frequencies, and adjusting the current responsive to the measured induced current components, until the measured induced components are below a predetermined threshold.

11. A method for tracking an object, comprising:
    driving a plurality of radiator coils with electrical currents at respective driving frequencies so as to generate a plurality of magnetic fields at the frequencies in a vicinity of an object being tracked;
    analyzing the currents flowing in the coils so as to measure, in each of the coils, induced current components at one or more of the frequencies of the other coils;
    adaptively adjusting the current driving each of the coils so as to include correction current components at the frequencies of the other coils, responsive to the measured induced current components, so that each of the coils generates a field substantially only at the respective driving frequency, wherein the correction current components are cancellation currents determined so as to substantially cancel parasitic magnetic fields generated by each of the coils in response to the magnetic fields generated by the other coils at the respective driving frequencies of the other coils;
    placing one or more sensor coils at a locatable site on the object; receiving signals generated by the sensor coils in response to the magnetic fields; and analyzing the signals to determine position and orientation coordinates of the object.

12. An object tracking system, comprising:

a plurality of radiator coils; and driver circuitry, coupled to drive the coils to generate magnetic fields at a plurality of driving frequencies, such that each of the coils is driven by a respective current that comprises a basic current at a respective one of the driving frequencies and cancellation currents at one or more of the other driving frequencies, so that each of the coils generates a field substantially only at the respective driving frequency, wherein cancellation currents are determined so as to substantially cancel pasitic magnetic fields generated by each of the coils in response to the magnetic fields generated by the dated by the other coils at the respective driving frequencies of the other coils;

one or more sensor coils, fixed to the object; and processing circuity, coupled to receive and analyze currents induced in the sensor coils due to the magnetec fields, so as to determine coordinates of the object.

* * * * *

UNITED STATES PATENT AND TRADEMARK OFFICE
CERTIFICATE OF CORRECTION

PATENT NO.   : 6,498,477 B1
DATED        : December 24, 2002
INVENTOR(S)  : Govari et al.

It is certified that error appears in the above-identified patent and that said Letters Patent is hereby corrected as shown below:

Column 10,
Line 3, "by the dated" should be deleted

Signed and Sealed this

Twenty-sixth Day of August, 2003

JAMES E. ROGAN
*Director of the United States Patent and Trademark Office*